United States Patent [19]

Sawyers et al.

[11] Patent Number: 4,828,387
[45] Date of Patent: May 9, 1989

[54] FILM MEASURING DEVICE AND METHOD WITH INTERNAL CALIBRATION TO MINIMIZE THE EFFECT OF SAMPLE MOVEMENT

[75] Inventors: Craig G. Sawyers, Letchworth; Laurence J. Robinson, Litlington, all of Great Britain

[73] Assignee: Ares-Serono Research & Development Limited Partnership, Boston, Mass.

[21] Appl. No.: 76,467

[22] Filed: Jul. 22, 1987

[30] Foreign Application Priority Data

Jul. 25, 1986 [GB] United Kingdom ............... 8618159

[51] Int. Cl.⁴ .......................... G01J 3/36; G01J 3/42
[52] U.S. Cl. ...................................... 356/319; 356/328
[58] Field of Search ................................ 356/328, 319

[56] References Cited

U.S. PATENT DOCUMENTS

| | | | |
|---|---|---|---|
| 3,985,442 | 10/1976 | Smith et al. | 356/328 X |
| 4,207,467 | 6/1980 | Doyle et al. | 250/338 |
| 4,525,066 | 6/1985 | Guillaume et al. | 356/43 |
| 4,664,522 | 5/1987 | LeFebre | 356/328 |
| 4,676,647 | 6/1987 | Kikkawa et al. | 356/328 X |

*Primary Examiner*—Vincent P. McGraw
*Attorney, Agent, or Firm*—Stephan P. Williams

[57] ABSTRACT

A method and apparatus for analysing the spectrum of light reflected by a reflecting structure (24) in which the effect upon the analysis results of variation in the angle between the reflecting structure and the incident beam (22) is minimised. The method and apparatus may utilise a dispersive element (26) constructed and arranged so as to minimise the effect of the variations. The method and apparatus may also utilise a calibration technique in which light with a known spectrum is reflected off the reflecting structure and analysed so that compensation may be made for the effect of the variation.

19 Claims, 11 Drawing Sheets

FILM MEASURING DEVICE AND METHOD WITH INTERNAL CALIBRATION TO MINIMIZE THE EFFECT OF SAMPLE MOVEMENT

This invention relates to spectrometers and in particular relates to methods of using spectrometers whereby potential errors can be compensated for and to apparatus for effecting such methods.

It is known that, under certain conditions, a reflecting structure such as a diffraction grating can strongly absorb light in a narrow range of wavelengths. The wavelength at which the maximum absorption notch occurs is a function of pitch, depth and shape of the grooves on the surface of the grating, and is also affected by any coating present on the grating surface. Thus, for example, if the grating surface has present thereon a thin layer of biologically sensitive material or other material capable of binding with a ligand, then if a first region of the surface is left as a standard (i.e. having an absorption wavelength of $\lambda_3$) and another region is treated with a liquid sample which contains the ligand then the complex formed by the binding of the ligand with the sensitive material on the grating surface will cause the absorption wavelength of the test region to shift from $\lambda_3$ to $\lambda_4$.

In principle this affords a method for assaying a sample to test for the presence of a ligand by a technique involving illuminating a reflecting structure under test at an oblique angle with a beam of polychromatic light, analysing the spectrum of the reflected light (for example by causing the reflected light to fall onto a multiple element linear photosensitive array) and determining whether there has been a shift, compared with a reference measurement, of the wavelength of light absorbed by the reflecting structure.

However, the wavelength absorbed by the reflecting structure is determined not only by the nature of the reflecting structure (e.g., where the structure is a diffraction grating, by the spacing and depth of grooves in the grating) but also by the angle of incidence of the light beam on the reflecting structure. The angle of incidence may vary due to movement of the reflecting structure relative to the beam, giving rise to potential errors.

In its broadest aspect, the present invention provides a method of analysing the spectrum of light reflected from a reflecting structure which comprises illuminating the reflecting structure at an oblique angle with a beam of polychromatic light and analysing the spectrum of the reflected light characterised by conducting the method in such a way as to minimise the effect upon the analysis result of variation in the angle between the reflecting structure and the beam of polychromatic light.

The present invention also provides apparatus comprising (i) a light source capable of producing a beam of polychromatic light; (ii) means for providing, in use, a beam of the polychromatic light at an oblique angle to a reflecting structure; (iii) means for analysing, in use, the spectrum of the reflected light; and (iv) means for minimising, in use, the effect upon the output of the analysing means of variation in the angle between the reflecting structure and the beam of polychromatic light.

The beam of polychromatic light will preferably be a diffraction limited collimated beam and will preferably be polarized.

According to one embodiment of the present invention, the effect on the output of the analysing means of variation in the angle between the reflecting structure and the beam of polychromatic light is minimised by imparting to the beam of polychromatic light at least one known spectral characteristic. Alternatively one or more reference beams of light each having at least one known spectral characteristic may be provided. The known spectral characteristic(s) is/are such as to enable the apparatus used to be calibrated.

For example, a light source may be employed which produces a diffraction limited collimated beam polarised perpendicularly relative to the plane of polarisation of the first light beam, so as to be unaffected by the surface plasmon resonance of a reflecting grating containing test and standard regions. The second light source is employed to introduce a known calibration feature in the spectrum incident on the reflection grating. This may be a characteristic of the light source itself, or may result from a combination of the source and a wavelength selective element. The image of the calibration features on the diode array provides sufficient information to wavelength-calibrate the system in both the test and reference regions.

If the spectrum from the second source has several calibration features, in the range $\lambda_1$ to $\lambda_2$, then the scaling factor in terms of wavelength per photosensitive element can be established.

By using the second source for calibration, it is possible to relax considerably the constraints on mechanical tolerances in the apparatus.

The light sources may be light emitting diodes (LEDs), laser light sources or incandescent bulbs.

If LEDs are employed, the light from the second light emitting diode is preferably caused to pass through a rare earth doped crystal such as neodymium doped yttrium aluminium garnet (NdYAG) or interference filters, which produces a good notch pattern in the range 700 to 850 nm.

If NdYAG is employed, the light emitting diode preferably emits light in a continuous band of wavelengths in the range 700 nm to 850 nm, having a midrange wavelength of the order of 775 nm.

According to a further embodiment of the invention the effect of the variation in the angle between the reflecting structure and the beam of polychromatic light on the output of the analysing means can be minimised by arranging for the reflected light to fall, prior to analysis, on a suitably constructed and arranged dispersive optical element, for example a blazed diffraction grating. Ideally, the dispersive element will be constructed and arranged so as to compensate exactly for the effect of variation in the angular orientation of the reflecting structure. In practice, the dispersive element will be constructed and arranged such that compensation is exact at a particular wavelength; the effect of the variation will then be minimal at neighbouring wavelengths.

Preferably the reflecting structure is a diffracting grating having a polycarbonate base having impressed or otherwise formed in the surface thereof a diffraction grating pattern of grooves coated by a thin light reflecting coating of gold, silver, aluminium or the like. The line spacing and depth of the grooves are selected so as to give the surface an absorption wavelength in the range 700 to 850 nm.

The reflecting structure may have present thereon a thin layer of material capable of binding with a ligand (for example an antigen or an antibody), enabling a sample to be assayed to detect for the presence or otherwise of the ligand in question. One region of the surface of the reflecting structure may be reserved as a standard or reference region; the sample is then applied to another region of the surface.

If the ligand is present in the sample it becomes bonded to the binding partner present on the reflecting structure. If no ligand is present in the sample the test region will have the same characteristics as the standard region and there should be no significant change in the position of the absorption notch as the test region replaces the standard region.

If on the other hand ligand is present in the sample, then some of the ligand in the sample will attach to the complementary binding partner on the reflecting surface and this will result in a shift in the position of the absorption notch due to the change in the surface parameters of the test region relative to the reference region, and this shift may be detected.

As mentioned above, the spectrum of the reflected light may be analysed by focussing the reflected light onto a multiple element linear photosensitive array, the wavelength of each component of the reflected light determining its position along the array. In such a case, the apparatus preferably further comprises electrical circuit means for scanning and interrogating the photosensitive array to determine the level of illumination, means for counting the positions of the elements from the start position of the scan, and means for recording and/or displaying an electrical signal corresponding to the absolute position of the notch in the final image or the shift in the notch position as between reference and test regions of the reflecting grating.

Typically the two light sources are combined into one optical path using a beam splitter.

The invention will now be described by way of example with reference to the accompanying drawings in which:

FIGS. 4 (a), (b) and (c) illustrate the output from the photodiode array when the reference area of a test grating is interrogated using the apparatus of FIG. 3.

FIGS. 5 (a), (b) and (c) illustrate the output from the photodiode array when the test area of a test grating is interrogated using the apparatus of FIG. 3.

Figure 1:
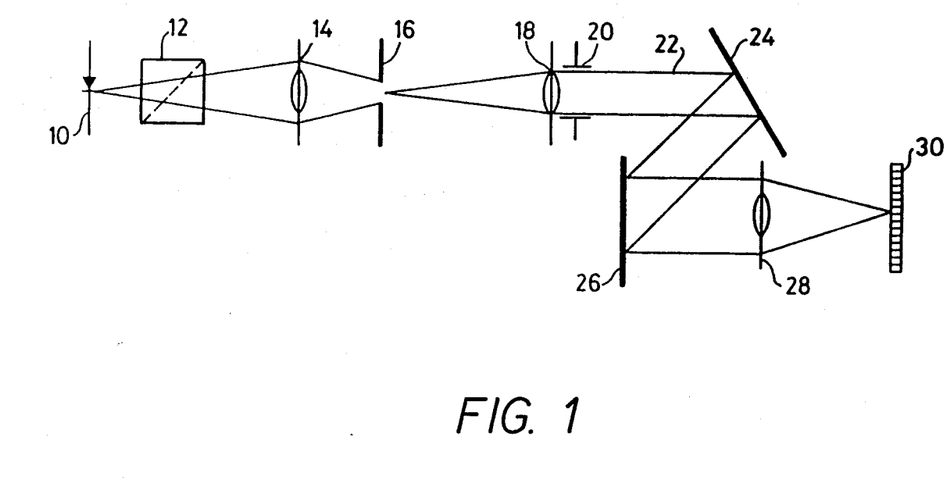
FIG. 1 illustrates one embodiment of apparatus according to the present invention.

In FIG. 1 a light emitting diode 10 having a band width of approximately 100 nm centred at approximately 775 nm supplies light for a polarising device 12 to a first lens 14 for illuminating a pin hole aperture 16, which may be a slit whose longer dimension is parallel to the grating lines of a diffraction grating to be described.

A lens 18 in combination with an aperture 20 produces a diffraction limited collimated beam of 3 mm diameter shown at 22.

The beam is directed towards reflecting diffraction grating 24 having on its surface a biologically active coating which will alter the surface parameters of the grating 24 in the presence of certain biochemical products. Thus the surface of the grating 24 may carry a layer of a particular antibody, eg Monoclonal antibody or may carry a layer of a particular antigen. If antibody material is on the grating surface, then the presence of corresponding antigen in a liquid sample applied to part of the surface of the grating will result in binding of the antigen to the antibody on the surface of the grating where the sample has been applied, which will in turn alter the surface characteristics of the grating surface in that region.

Although not shown, means is provided for moving the grating 24 so as to present first the reference region (i.e. untreated region) to the beam 22 and then the treated region.

The light reflected by the coated reflecting diffraction grating 24 is analysed by a blazed reflection grating 26 and another lens 28 which forms an image on a linear array of photodiodes 30.

Typically the array has 256 elements each approximately 25 micrometers by 2.5 mm.

Using a blazed diffraction grating having 800 lines per mm, and a 75 mm focal length lens at 28, a wavelength range of 100 nm can be obtained over the 256 elements in the array 30.

If light extending over a waveband of greater than 100 nm and centred at approximately 800 nm is incident on the grating 26, then all of the photodiodes are illuminated.

The apparatus seeks to determine the presence and position of an absorption first for the reference or standard region of the reflecting grating 24 and then for the treated area after application of the sample and possible consequential antibody-antigen binding, so as to determine the extent of the shift occasioned by the binding and consequential build-up of material on the surface of the reflecting grating 24.

Although not shown, scanning and detecting circuitry is associated with the line of photodiodes 30 so that electrical signals indicative of the presence and absence of light on the photdiodes can be derived and processed as by counting and curve fitting, to determine the position of the spectral minimum from a start position in the array thereby, after calibration, enabling the precise wavelength of the notch to be determined.

The precise position of the notch (if present) in the array 30 is determined not only by the parameters of the surface of the grating 24 but is also determined by the angle of incidence of the beam 22 on the grating 24. Since it is necessary to move either the beam or the grating relative the one to the other so as to cause the beam to impinge on first the standard region of the grating and then on the treated region of the grating, it will be appreciated that there is a significant chance that the orientation of the grating 24 when the treated region is in position may be different from the orientation of the grating when the standard or reference region is in position.

In order to overcome this problem, the parameters of the grating 26 may be chosen so as to compensate for any orientation shift in the grating 24 provided such shifts are relatively small. In this event, the apparatus as shown in FIG. 1 can be calibrated to provide an absolute readout from the array 30 since under normal circumstances the only shift which will occur between standard and treated regions of the grating 24 will be due to the build-up of material on the treated region due to antibody-antigen binding.

The parameters of the grating 26 needed to minimise the effect upon the output of the spectrometer of variation of the angle between the beam of polychromatic light and the grating 24 may be calculated (with reference to FIG. 7) as follows.

Figure 7:
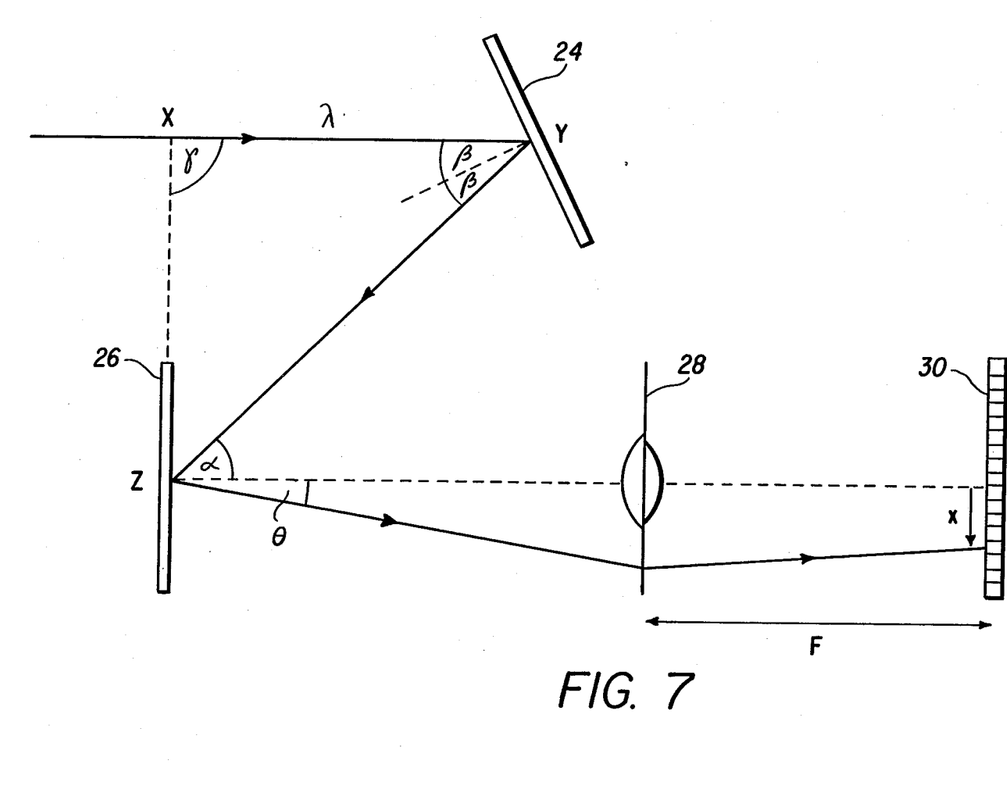
FIG. 7 illustrates the coordinate system used to determine how a blazed diffraction grating may be constructed and arranged so as to minimise the effect of variation in the angle of incidence at a reflecting diffraction grating.

Consider light of wavelength $\lambda$ incident on the grating 24 at an angle of $\beta$ to the normal. This light is reflected from grating 24 onto blazed diffraction grating 26 upon which it is incident at an angle of $\alpha$. From blazed diffraction grating the light is reflected towards lens 28 at an angle of $\theta$ to the normal of blazed diffraction grating 26. The light is then focused by lens 28 to a point on the array 30 a distance x from the principal axis of lens 28. The following parameters are used to describe the features of the optical system illustrated in FIG. 7:

Do is the periodicity of the grating 24
D is the periodicity of the blazed diffraction grating 26
$\theta$ is the angle between the normal to the blazed diffraction grating 26 and the light reflected from it.
$\theta_o$ is the angle between the normal to the blazed diffraction grating 26 and the principal axis of lens 28 measured in the same sense as $\theta$.
f is the focal length of lens 28.
C is a constant which is characteristic of the SPR effect on grating 24 and changes if the nature of grating 24 is changed e.g. by the binding of a thin layer of particles.
$\gamma$ is the angle between the incident beam of light and the plane of blazed diffraction grating 26.

If $\lambda$ is such that SPR is excited then $$\lambda/Do - \sin\beta = C \qquad \text{Equation 1}$$

The first order dispersive action of the blazed diffraction grating 26 is described by $$D(\sin\theta + \sin\alpha) = \lambda \qquad \text{Equation 2}$$

Since the array 30 is in the focal plane of lens 28 then
$$x = f\tan(\theta - \theta_o) \qquad \text{Equation 3}$$

The direction of the incident light beam to the grating 24 and the orientation of blazed diffraction grating 26 are both constant and therefore from triangle XYZ in FIG. 7 it can be seen that $$\gamma + 2\beta + \pi/2 - \alpha = \pi$$

$$\alpha = 2\beta + \gamma - \pi/2 \qquad \text{Equation 4}$$

In order to minimise the effect of the variations, the parameters of the grating must be chosen such that $$dx/d\beta = dx/d\theta \cdot d\theta/d\beta = O \qquad \text{Equation 5}$$

Differentiating Equation 3 by $\theta$ $$dx/d\theta = f\sec^2(\theta - \theta_o) \qquad \text{Equation 6}$$

Equations 1 and 2 imply $$D(\sin\theta + \sin\alpha) = Do(C + \sin\beta)$$

$$\sin\theta = Do/D(C + \sin\beta) - \sin\alpha \qquad \text{Equation 7}$$

Equations 4 and 7 imply $$\sin\theta = Do/D(C + \sin\beta) - \sin(2\beta + \gamma - \pi/2) \qquad \text{Equation 8}$$

Differentiating Equation 8 by $\beta$ $$\cos\theta \, d\theta/d\beta = Do/D \cos\beta - 2\cos(2\beta + \gamma - \pi/2) \qquad \text{Equation 9}$$

Equations 5, 6 and 9 imply $$dx/d\beta = f\sec^2(\theta - \theta_o) \cdot \sec\theta(Do/D\cos\beta - 2\cos(2\beta + \gamma + \pi/2)$$

Thus $dx/d\beta = O$ if $Do/D\cos\beta - 2\cos(2\beta + \gamma - \pi/2) = O$ which is equivalent to $$Do/2D \cos\beta = \cos\alpha \qquad \text{Equation 11}$$

Hence in order that the blazed diffraction grating 26 should minimise the effect of variation in the angle between the beam of polychromatic light and the grating 24 grating 26 should be constructed and arranged such that the values of D and $\alpha$, satisfy Equation 11.

Figure 2:
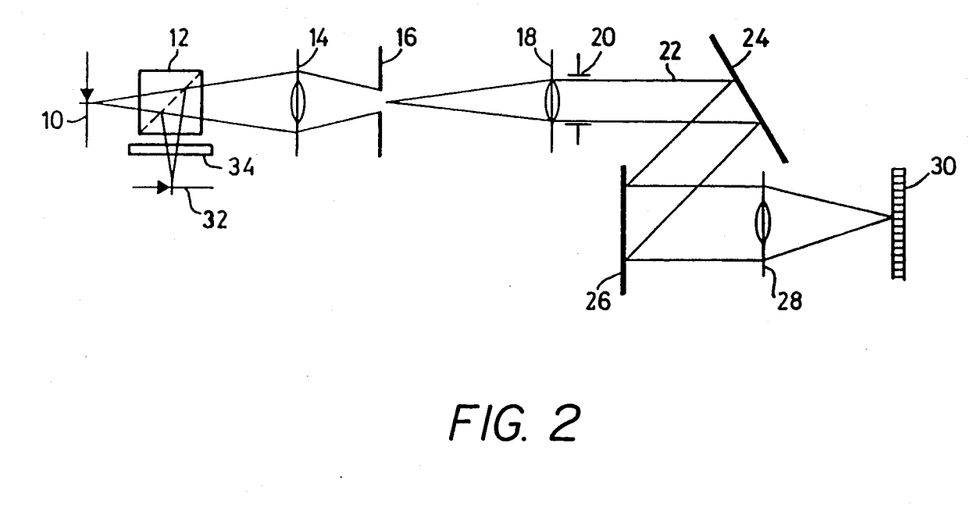
FIG. 2 illustrates a second embodiment of apparatus according to the present invention.

An alternative and preferred arrangement is shown in FIG. 2 in which a second light emitting diode 32 is provided together with a rare earth doped crystal filter 34, eg NdYAG. The filter has a well defined absorption characteristic so as to provide a good notch pattern in the waveband of interest and since these notches are of constant wavelength and their existence is not dependent on the absorption characteristics of the surface of the grating 24, this notch pattern, produced by the filter 34, can be used to calibrate the instrument.

Since it is not necessary to use the surface 24 in its surface plasmon mode to monitor the calibration notches, the light from the filter 34 may be polarised orthogonally relative to the plane of polarisation of the light from the light emitting diode 10 so that it is simply reflected by the surface of the grating 24 onto the analysing grating 26.

If the filter 34 produces two well defined notches in the waveband of interest then full calibration of the photodiode array 30 can be achieved since with the notches occurring at two known wavelengths, not only can the absolute position along the array for any wavelength be determined but also the wavelength change per photodiode spacing can be determined.

The apparatus shown in FIG. 2 will normally be operated so that the calibration light emitting diode 32 is operated whilst the reference area of the grating 24 is in position and then again after the test area has been located in position. In each case, after calibration, the light emitting diode 32 can be turned off and the light emitting diode 10 turned on so as to enable analysis of the light from the reflecting surface 24 to be performed.

Figure 3:
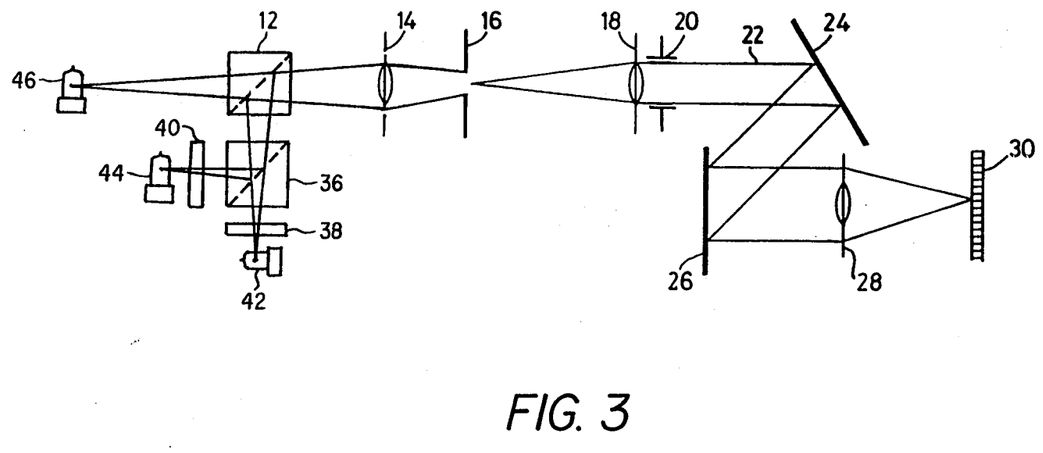
FIG. 3 illustrates a third embodiment of apparatus according to the present invention.

A further alternative and preferred arrangement is shown in FIG. 3 in which LED 10 is replaced by an incandescent bulb 46 and the second light source comprises incandescent bulbs 42 and 44, wavelength filters 38 and 40 and beam splitter 36. Filters 38 and 40 have different, well defined, absorption characteristics which provide good notch patterns in the waveband of interest. As in the embodiment above, since the notch patterns produced by filters 38 and 40 are constant and are not dependent upon the parameters of grating 24 this second light source can be used to calibrate the apparatus.

The calibration technique is as described for the embodiment shown in FIG. 2 except that the two calibration notches produced by bulb 44 and filter 40 and bulb 42 and filter 38 respectively may be produced independently of each other. So, for example, in use bulb 42 and filter 38 could be used to produce a first calibration notch of known wavelength which is detected by array 30 and then bulb 44 and filter 40 could be used to produce a second calibration notch of known wavelength to be detected by array 30. With the position on array 30 of these two known wavelengths having been determined then when bulb 46 is illuminated to excited surface plasmon resonance (SPR) on grating 24 the absolute value of the wavelength of light absorbed can be determined.

However, since it is not necessary to excite SPR on grating 24 to monitor the calibration notches then the light from bulbs 42 and 44 may be polarised orthogonally to the light from bulb 46. This has the advantage that the calibration notch patterns are not complicated by absorption caused by SPR at grating 24.

Figure 4A:
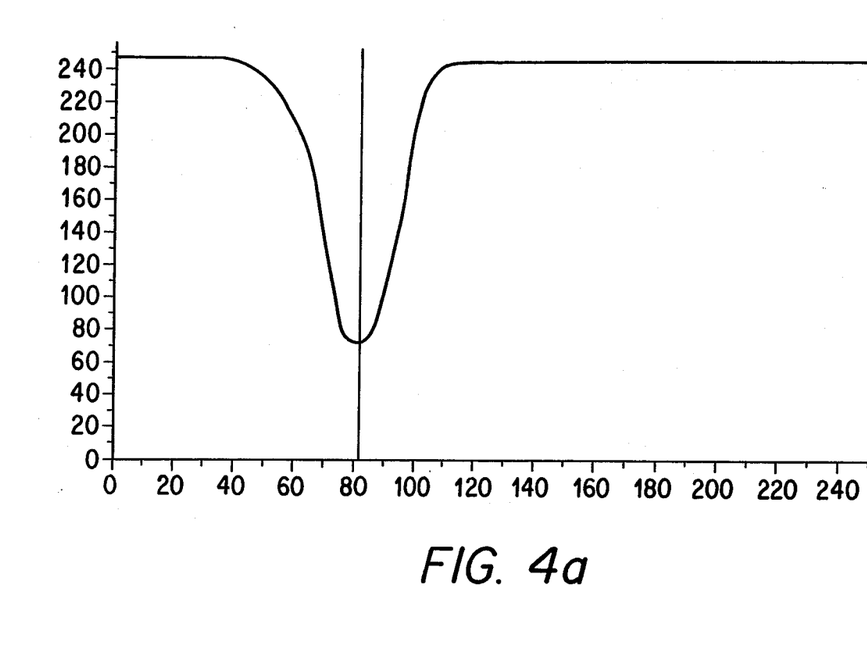
Figure 4B:
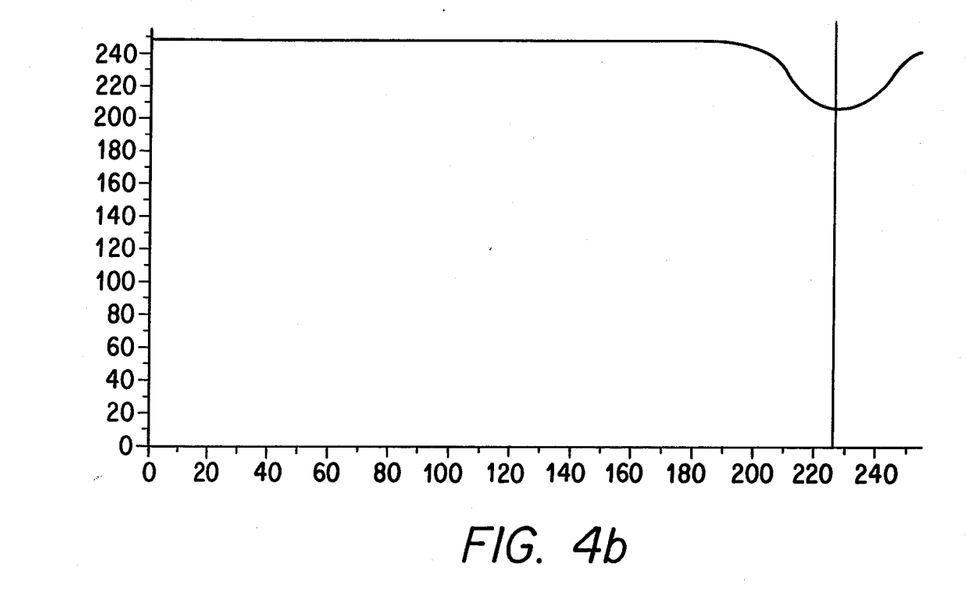

FIGS. 4(a) and 4(b) show the output from the photodiode array when the bulbs 42 and 44 respectively are operated and the reference area of the test grating is in position. The filter notch minima are found, using a curve fitting algorithm, to occur at 81,81 and 225,71 pixels respectively.

Figure 4C:
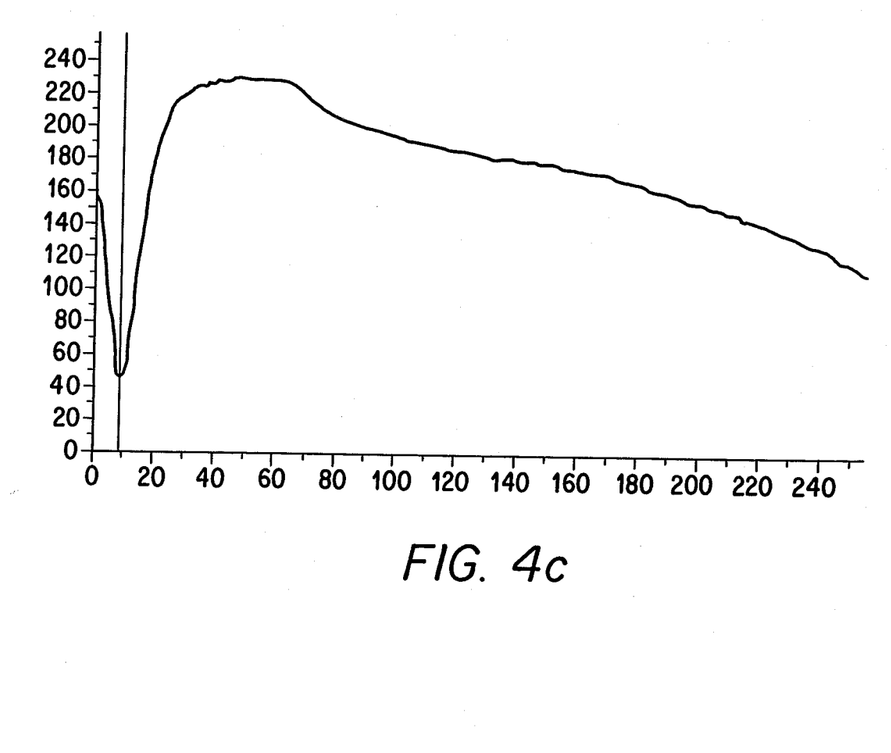

FIG. 4(c) shows the plasmon resonance spectrum of the reference area of the test grating when bulb 46 is operated. The SPR occurs at 9,37 pixels. The resonance minimum can be found to be at 735.29 nm by this calibration assuming the calibration notch filter minima are of wavelengths of 767 nm and 830 nm.

Figure 5A:
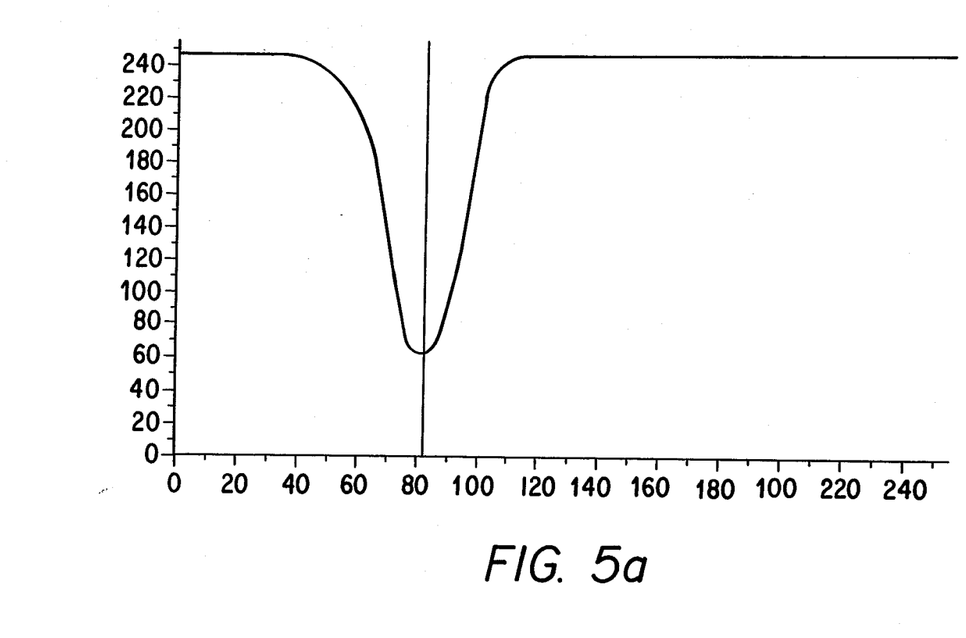
Figure 5B:
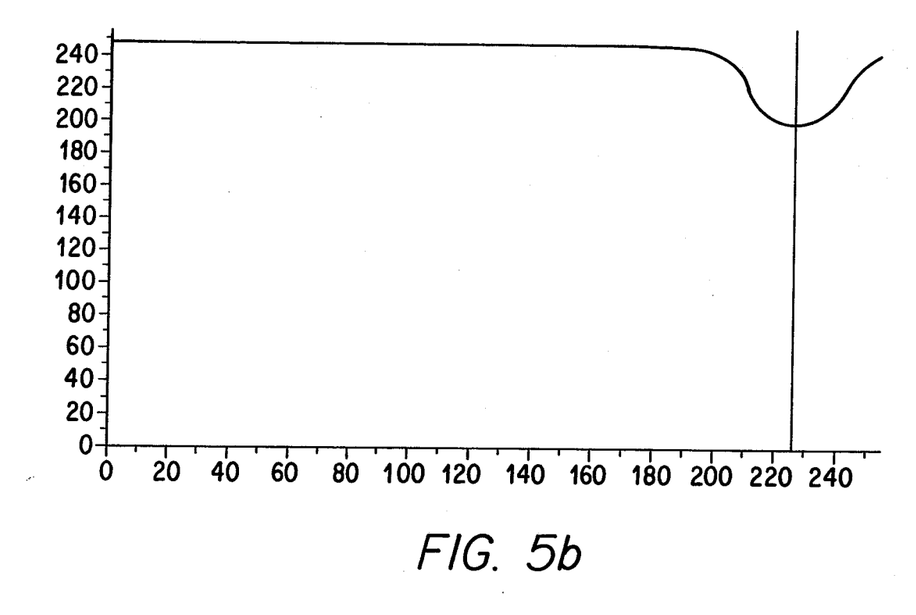

FIGS. 5(a) and 5(b) show the output from the photodiode array when the light source 32 is operated and the test area of the test grating is in position and an antobody/antigen interaction has occurred. The filter notch minima are now found to occur at 81,74 and 225,72 pixels respectively.

Figure 5C:
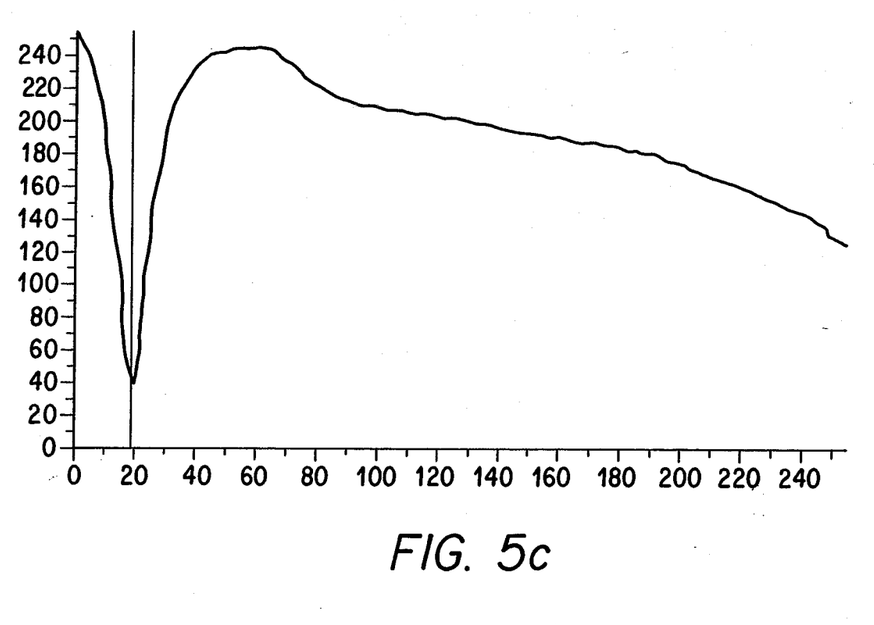

FIG. 5(c) shows the related plasmon resonance spectrum, where the minimum is found at 19,33 pixels which is equivalent to a resonance minimum at 739.69 nm. A plasmon resonance shift of 4.40 nm has thus occurred indicating the binding of antibody to antigen in the test area.

According to one embodiment of the invention there is provided apparatus for detecting the presence of a thin coating of material on the surface of a reflecting diffraction grating comprising:

(1) a light source for producing a beam of polarised light having a continuous spectrum of wavelengths at least between $\lambda_1$ and $\lambda_2$, (2) first lens means producing a diffraction limited collimated beam of small diameter, incident on the reflecting diffraction grating under test, (3) a blazed diffraction grating adapted to receive light reflected by the reflecting grating, (4) second lens means for focusing the reflected light onto a multiple element linear photodiode array, the wavelength of each component of the light reflected by the blazed diffraction grating determining its position along the linear photodiode array, and the array length being sufficient to encompass the range of positions determined by the two wavelengths $\lambda_1$ and $\lambda_2$, (5) means for establishing relative movement between the light beam and the reflecting grating to permit different regions of the grating to serve as the reflecting surface, wherein the absorption wavelength $\lambda_3$ of the reflecting grating is in the range $\lambda_1$ to $\lambda_2$, so that light of wavelength $\lambda_3$ is missing from the light incident on the blazed diffraction grating and therefore from the spectrum of light incident on the linear array, so that one or more of the photodiodes receives no light; and means is provided for determining the signal output from each of the elements of the linear array in turn, to determine which of the elements is receiving no light, to determine by calibration, the wavelength of the light absorbed by the surface of the reflecting grating.

The following Examples illustrate the method of the present invention and its use in an assay.

EXAMPLE 1

OPERATION OF THE CALIBRATION NOTCHES

Preparation of Metallised Diffraction Gratings

Polycarbonate diffraction gratings (pitch=633 nm, depth=30 nm) were fabricated by injection moulding. A layer, 10 nm thick, of chromium was deposited onto the undulating surface of the grating by vacuum evaporation. The function of this layer is to promote the adhesion of a gold layer onto the grating structure and it plays no part in the generation of surface plasmon resonance. A film of gold, 90 nm thick, was then deposited on top of the chromium, also by vacuum evaporation techniques.

Measurement of the Position of the SPR Absorption

The metallised diffraction gratings were positioned in an instrument comprising the components as shown in FIG. 3. Eight zones on each of 49 gratings were read sequentially in the following manner:

The grating was illuminated with light passing through calibration filter 38 (minimum light intensity at 767 nm).

The grating was illuminated with light passing through calibration filter 40 (minimum light intensity at 830 nm).

The grating was illuminated with white light to enable the position of the SPR absorption to be measured.

In all cases the position of the lowest intensity of reflected light was recorded as a pixel position on the photodiode array. The exact position of the point of least intensity of reflected light was calculated using a curve fitting algorithm.

The pixel position of the calibration notches enabled the photodiode array to be calibrated for the actual angle of incidence of light onto the particular zone of grating being interrogated, thus compensating for variations in the position of the SPR absorption due to any misalignments of the grating in the instrument.

Results

The data from these measurements on 49 gratings are presented in Table 1. As can be seen from the coefficient of variation in the position of the SPR absorption before and after correction (i.e. the pixel position and the wavelength values respectively) the error in measurement of the position of the SPR absorption is greatly reduced.

TABLE 1

| | Position of Notch 1 (pixels) | Position of Notch 2 (pixels) | Position of Anomaly (pixels) | Position of Anomaly (nm) |
|---|---|---|---|---|
| Average | 74.00 | 223.96 | 10.74 | 736.67 |
| Standard Deviation | 1.45 | 1.35 | 2.08 | 0.91 |
| Coefficient of variation | 1.96% | 0.60% | 19.40% | 0.12% |
| Range | 12.25 | 10.28 | 12.06 | 5.83 |

EXAMPLE 2

DETECTION OF INFLUENZA VIRUS IN AN ASSAY WHICH USES THE CALIBRATION NOTCHES

Preparation of Reagents

Metallised diffraction gratings were prepared as described previously. A mouse monoclonal antibody against influenza virus haemagglutinin was prepared in the usual way and purified from ascites fluid by affinity chromatography. A mouse polyclonal anti-IgG antibody was obtained from the Sigma Chemical Company, London. Influenza A virus was cultured in hens eggs using standard methods (see, for example, Diagnostic Procedures for Viral, Rickettsial and Chlamydial Infections, 5th Edition, edited by E. H. Lennette and N. J. Schmidt, American Public Health Association, Washington DC., 1979).

Method of Performing the Test

The metallised diffraction gratings were preread in a spectrometer instrument which incorporated the calibration notches after which antibody, either anti-influenza antibody or anti-IgG antibody was immobilised onto the metallised grating by adsorption. Antibody was made up to a final concentration of 100 ug/ml in phosphate buffered saline (PBS) (50 mM $PO_4^{2-}$-pH 7.4 containing 0.9% NaCl). 250 $\mu$l of this solution (ether anti-influenza or anti-IgG antibody) was applied evenly to the diffraction grating and incubated for 30 minutes at 37° C after which the gratings were washed with PBS (6 times), PBS containing 0.05% w/v of the detergent Tween 20 (PBST) (3 times) and PBS containing casein hydrolysate (0.1% w/v) (3 times). Excess liquid was removed from the grating and diluted virus pipetted onto the gratings (coated with either the anti-influenza or the anti-IgG antibody) which were then left to incubate for 30 minutes at 37° C. During both incubations care was taken to ensure that the solutions did not dry out.

After the second incubation, the gratings were washed with PBST (6 times), PBS (6 times) and deionised, distilled water (6 times). The gratings were then dried in a semi-upright position, draining into tissue and were left for 20 minutes at 37° C. The gratings were read as previously described and in the same order as the initial reading. This enabled the shift in the position of the SPR absorption, due to the adsorption of antibody onto the grating and the specific interaction between the virus and the anti-influenza antibody, to be measured and differentiated from the non-specific binding of the virus to the diffraction grating as measured by the gratings coated with anti-IgG antibody.

Results

Figure 6:
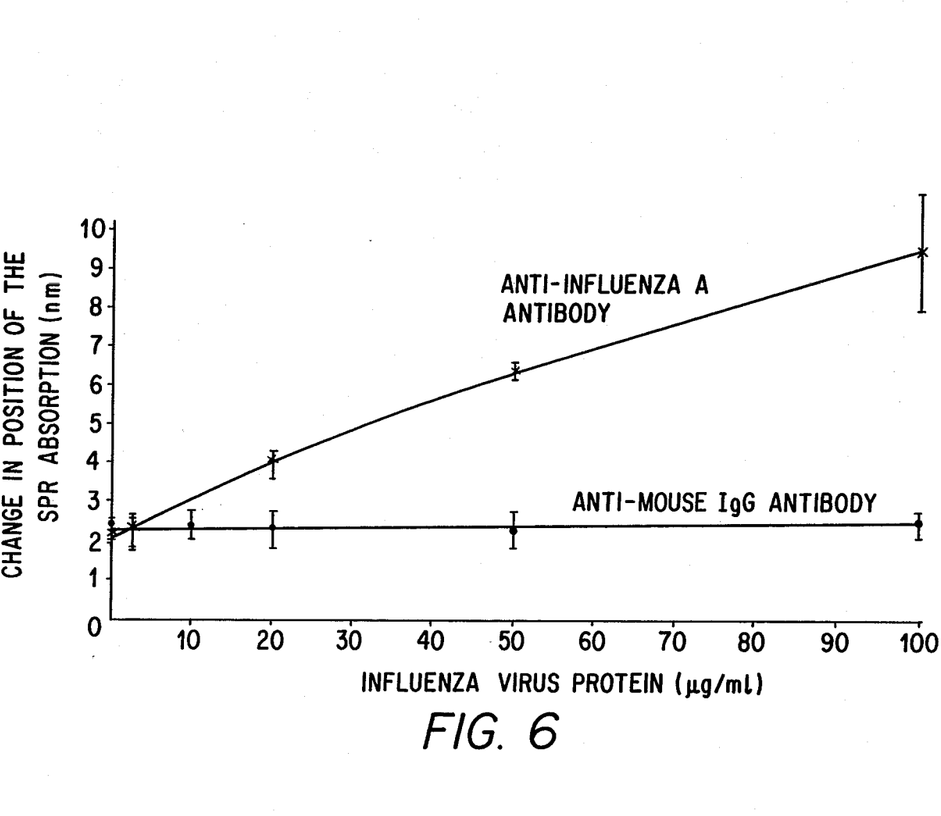
FIG. 6 is a graph plotting the results of an assay performed using apparatus according to the present invention.

The results shown in FIG. 6, in which each point is calculated as the mean of three slides, clearly indicate that there is a shift in the position of the SPR absorption on the binding of the influenza virus to the anti-influenza antibody on the test strip and this shift is much greater than the shift in the SPR absorption position due to the non-specific binding of the virus to the anti-IgG coated gratings.

We claim:

1. Apparatus for detecting the presence of a thin coating of material on the surface of a reflecting diffraction grating comprising:
   (1) a light source for producing a beam of polarised light having a continuous spectrum of wavelengths at least between $\lambda_1$ and $\lambda_2$,
   (2) first lens means producing a diffraction limited collimated beam of small diameter, incident on the reflecting diffraction grating under test,
   (3) a blazed diffraction grating adapted to receive light reflected by the reflecting grating,
   (4) second lens means for focusing the reflected light onto a multiple element linear photodiode array, the wavelength of each component of the light reflected by the blazed diffraction grating determining its position along the linear photodiode array, and the array length being sufficient to encompass the range of positions determined by the two wavelengths $\lambda_1$ and $\lambda_2$,
   (5) means for establishing relative movement between the light beam and the reflecting grating to permit different regions of the grating to serve as the reflecting surface, wherein the absorption wavelength $\lambda_3$ of the reflecting grating is in the range $\lambda_1$ to $\lambda_2$, so that light of wavelength $\lambda_3$ is missing from the light incident on the blazed diffraction grating and therefore from the spectrum of light incident on the linear array, so that one or more of the photodiodes receives no light; and means for determining the signal output from each of the elements of the linear array.

2. In a method of detecting the presence of a thin film on the surface of a reflecting diffraction grating which comprises alternately illuminating a reference portion and a test portion of the reflecting diffraction grating at an oblique angle with a beam of polychromatic light and analyzing the spectrum of the reflected light, the improvement wherein any variation in the angle between the reflecting diffraction grating and the beam of polychromatic light is factored into the analysis by imparting at least one known spectral characteristic to either the beam of polychromatic light or to one or more reference beams of light which alternately illuminate the reference and test portions of the reflecting diffraction grating.

3. The method of claim 2 wherein the known spectral characteristic comprises at least one absorption notch pattern within the range of 700 to 850 nm.

4. The method of claim 3 wherein the one or more reference beams of light are polarized such that the reflecting diffraction grating does not affect their spectra.

5. The method of claims 2, 3 or 4 wherein the reflected light, prior to analysis, is disposed by a blazed diffraction grating.

6. The method of claim 5 wherein the blazed diffraction grating is constructed and arranged to minimize the effect upon the analysis of any variation in the angle between the reflecting diffraction grating and the beam of polychromatic light.

7. The method of claim 5 wherein the beam of polychromatic light is polarized such that the reflecting diffraction grating will have maximum effect upon the spectrum of reflected light.

8. The method of claim 7 wherein the film to be detected is a biologically active material.

9. The method of claim 8 wherein the blazed diffraction grating is constructed and arranged such that $$Do/2D \cos\beta = \cos\alpha$$

wherein Do is the periodicity of the reflecting diffraction grating, D is the periodicity of the blazed diffraction grating, $\beta$ is the angle to the normal of incident light on the reflecting diffraction grating, and $\alpha$ is the angle to the normal of incident reflected light on the blazed diffraction grating.

10. In a method of detecting the presence of a thin film on the surface of a reflecting diffraction grating which comprises alternately illuminating a reference portion and a test portion of the reflecting diffraction grating at an oblique angle with a beam of polychromatic light and analyzing the spectrum of the reflected light, the improvement wherein the effect on the analysis of any variation in the angle between the reflecting diffraction grating and the beam of polychromatic light is minimized by dispersing the reflected light, prior to analysis, with a blazed diffraction grating which is constructed and arranged such that $$Do/2D \cos\beta = \cos\alpha$$

wherein Do is the periodicity of the reflecting diffraction grating, D is the periodicity of the blazed diffraction grating, $\beta$ is the angle to the normal of incident light on the reflecting diffraction grating, and $\alpha$ is the angle to the normal of incident reflected light on the blazed diffraction grating.

11. Apparatus for detecting the presence of a thin film on the surface of a reflecting diffraction grating which comprises (i) a light source capable of producing a beam of polychromatic light; (ii) means for alternately illuminating a reference portion and a test portion of the reflecting diffraction grating at an oblique angle with a beam of the polychromatic light; (iii) means for analyzing the spectrum of the reflected light; and (iv) means for factoring into the analysis any variation in the angle between the reflecting diffraction grating and the beam of polychromatic light which includes means for imparting at least one known spectral characteristic to either the beam of polychromatic light or to one or more reference beams of light which alternately illuminate the reference and test portions of the reflecting diffraction grating.

12. The apparatus of claim 11 which includes means for providing, as the known spectral characteristic, at least one absorption notch pattern within the range of 700 to 850 nm.

13. The apparatus of claim 12 which includes means for polarizing the beam of polychromatic light and/or the one or more reference beams of light.

14. The apparatus of claim 13 wherein the means for providing a beam of polychromatic light comprises means for providing a diffraction limited collimated beam.

15. The apparatus of claim 14 wherein the analyzing means comprises a multiple element linear photosensitive array.

16. The apparatus of claim 15 further comprising means for scanning and interrogating the photosensitive array to determine the level of illumination at elemental positions therealong.

17. The apparatus of claim 16 wherein the means for providing the absorption notch pattern is a rare earth doped crystal.

18. The apparatus of claims 11, 12, 13, 14, 15, 16 or 17 which comprises a blazed diffraction grating positioned to disperse reflected light from the reflecting diffraction grating prior to analysis.

19. The apparatus of claim 18 wherein the blazed diffraction grating is constructed and arranged such that $$Do/2D \cos\beta = \cos\alpha$$

wherein
Do is the periodicity of the reflecting diffraction grating, D is the periodicity of the blazed diffraction grating, $\beta$ is the angle to the normal of incident light on the reflecting diffraction grating, ps and $\alpha$ is the angle to the normal of incident reflected light on the blazed diffraction grating.

* * * * *

UNITED STATES PATENT AND TRADEMARK OFFICE
CERTIFICATE OF CORRECTION

PATENT NO. : 4,828,387

DATED : May 9, 1989

INVENTOR(S) : Craig G. Sawyers and Laurence J. Robinson

It is certified that error appears in the above-identified patent and that said Letters Patent is hereby corrected as shown below:

In claim 5, line 2 "disposed" should read --dispersed--. In claim 19, line 9, "ps" should be deleted.

Signed and Sealed this

Twentieth Day of February, 1990

*Attest:*

JEFFREY M. SAMUELS

*Attesting Officer*  *Acting Commissioner of Patents and Trademarks*